(12) United States Patent
Dafni (10) Patent No.: US 8,718,227 B2
(45) Date of Patent: *May 6, 2014

(54) GRADED RESOLUTION FIELD OF VIEW CT SCANNER

(75) Inventor: Ehud Dafni, Caesarea (IL)

(73) Assignee: Arineta Ltd., Caesarea (IL)

( * ) Notice: Subject to any disclaimer, the term of this patent is extended or adjusted under 35 U.S.C. 154(b) by 221 days.

This patent is subject to a terminal disclaimer.

(21) Appl. No.: 13/342,040

(22) Filed: Jan. 1, 2012

(65) Prior Publication Data

US 2012/0106696 A1 May 3, 2012

Related U.S. Application Data

(62) Division of application No. 11/921,238, filed as application No. PCT/IB2006/051737 on May 31, 2006, now Pat. No. 8,111,804.

(60) Provisional application No. 60/685,418, filed on May 31, 2005.

(51) Int. Cl.
*A61B 6/03* (2006.01)

(52) U.S. Cl.
USPC .................................. 378/19; 378/4

(58) Field of Classification Search
USPC ....................................... 378/4–20
See application file for complete search history.

(56) References Cited

U.S. PATENT DOCUMENTS

| | | |
|---|---|---|
| 3,973,128 A | 8/1976 | LeMay |
| 5,105,087 A | 4/1992 | Jagiclinski |
| 5,355,309 A | 10/1994 | Eberhard et al. |
| 6,633,627 B2 | 10/2003 | Horiuchi |
| 6,658,082 B2 * | 12/2003 | Okumura et al. ............... 378/19 |
| 7,522,695 B2 * | 4/2009 | Nishide et al. .................... 378/4 |
| 2002/0176530 A1 | 11/2002 | Okumura et al. |
| 2003/0068005 A1 | 4/2003 | Yamazaki |
| 2005/0105678 A1 | 5/2005 | Nakashima |
| 2006/0002508 A1 * | 1/2006 | Yahata ........................... 378/19 |
| 2007/0019779 A1 | 1/2007 | Nishide et al. |
| 2010/0215142 A1 | 8/2010 | Dafni et al. |

FOREIGN PATENT DOCUMENTS

| | | |
|---|---|---|
| DE | 19524858 | 1/1997 |
| DE | 19600115 | 1/1997 |
| DE | 10150428 | 4/2003 |

(Continued)

OTHER PUBLICATIONS

Communication Relating to the Results of the Partial International Search Dated Mar. 22, 2007 From the International Searching Authority Re.: Application No. PCT/Ib2006/051737.

(Continued)

*Primary Examiner* — Hoon Song (57) ABSTRACT

A CT scanner comprising: a rotor rotatable about an axis of rotation: an X-ray source mounted to the rotor having a focal spot from which an X-ray beam emanates; an X-ray detector array comprising a plurality of X-ray detectors for detecting X-rays in the X-ray beam; wherein the detector array has at least one high resolution region in which detectors have a high packing density and at least one low resolution region in which detectors have a low packing density and are separated by X-ray insensitive regions substantially larger than insensitive regions resulting from septa between detectors that function to reduce detector cross talk.

23 Claims, 8 Drawing Sheets

(56) References Cited

FOREIGN PATENT DOCUMENTS

| EP | 0856748 | 8/1998 |
|---|---|---|
| WO | WO 2004/023123 | 3/2004 |
| WO | WO 2005/071392 | 8/2005 |
| WO | WO 2006/129282 | 12/2006 |

OTHER PUBLICATIONS

International Preliminary Report on Patentability Dated Dec. 6, 2007 From the International Bureau of WIPO Re.: Application No. PCT/IB2006/051737.
Communication Pursuant to Article 94(3) EPC Dated Oct. 7, 2010 From the European Patent Office Re.: Application No. 06745054.4.
Communication Pursuant to Article 94(3) EPC Dated Oct. 9, 2008 From the European Patent Office Re.: Application No. 06745054.4.
International Search Report and the Written Opinion Dated Sep. 11, 2007 From the International Searching Authority Re.: Application No. PCT/IB2006/051737.
Notice of Allowance Dated Oct. 31, 2011 From the US Patent and Trademark Office Re. U.S. Appl. No. 11/921,238.
Office Action Dated Aug. 1, 2010 From the Israel Patent Office Re.: Application No. 187780 and Its Translation Into English.
Office Action Dated Mar. 3, 2010 From the Israel Patent Office Re.: Application No. 187780 and Its Translation Into English.
Office Action Dated Aug. 14, 2011 From the Israel Patent Office Re.: Application No. 187780 and Its Translation Into English.
Official Action Dated Jun. 16, 2011 From the US Patent and Trademark Office Re. U.S. Appl. No. 11/921,238.
Official Action Dated Apr. 19, 2011 From the US Patent and Trademark Office Re. U.S. Appl. No. 11/921,238.
Official Action Dated Jan. 19, 2011 From the US Patent and Trademark Office Re. U.S. Appl. No. 11/921,238.
Official Action Dated Aug. 23, 2010 From the US Patent and Trademark Office Re. U.S. Appl. No. 11/921,238.
Response Dated Sep. 14, 2011 to Official Action of Jun. 16, 2011 From the US Patent and Trademark Office Re. U.S. Appl. No. 11/921,238.
Response Dated Jun. 2, 2011 to Official Action of Apr. 19, 2011 From the US Patent and Trademark Office Re. U.S. Appl. No. 11/921,238.
Response Dated Feb. 7, 2011 to Communication Pursuant to Article 94(3) EPC of Oct. 7, 2010 From the European Patent Office Re.: Application No. 06745054.4.
Response Dated Apr. 13, 2011 to Official Action of Jan. 19, 2011 From the US Patent and Trademark Office Re. U.S. Appl. No. 11/921,238.
Response Dated Oct. 14, 2010 to Office Action of Aug. 1, 2010 From the Israel Patent Office Re.: Application No. 187780.
Response Dated Sep. 22, 2010 to Official Action of Aug. 23, 2010 From the US Patent and Trademark Office Re. U.S. Appl. No. 11/921,238.
Response Dated Jun. 29, 2010 to Office Action of Mar. 3, 2010 From the Israel Patent Office Re.: Application No. 187780.

* cited by examiner

GRADED RESOLUTION FIELD OF VIEW CT SCANNER

RELATED APPLICATIONS

This Application is a divisional of U.S. patent application Ser. No. 11/921,238 filed on Nov. 29, 2007, which is a National Phase of PCT Patent Application No. PCT/IB2006/051737 having International Filing Date of May 31, 2006, which claims the benefit of priority under USC 119(e) of U.S. Patent Application No. 60/685,418 filed on May 31, 2005. The contents of the above applications are all incorporated herein by reference.

FIELD OF THE INVENTION

The present invention relates to computerized tomography (CT) X-ray imaging and to CT scanners having fields of view (FOVs) adapted for imaging limited volumes of tissue within a patient's body.

BACKGROUND OF THE INVENTION

In CT X-ray imaging of a patient, X-rays are used to image internal structure and features of a region, an "imaging region", of the patient's body. The imaging is performed by a CT scanner comprising an X-ray source that provides an X-ray beam and an array of closely spaced X-ray detectors facing a region, referred to as a "focal spot", of the X-ray source from which the beam emanates. The X-ray beam is a substantially "fan-shaped" X-ray beam if the scanner acquires at any given time data for imagining only a single "slice" or a small number of slices of the imaging region of a patient. The beam is a "cone-shaped" X-ray beam if the scanner acquires data for imaging a relatively large number, generally more than about 10, slices of a patient's imaging region. A scanner comprising a fan beam is generally referred to as a single slice scanner and a scanner comprising a cone beam is generally referred to as a multislice scanner. Many of the modern day scanners are multislice scanners and the discussion hereinafter generally refers to multislice scanners with obvious modifications where necessary to encompass single slice scanners.

The X-ray source and array of detectors are mounted in a gantry so that an imaging region of a person being imaged with the CT scanner can be positioned in a field of view (FOV) of the scanner that is located within the gantry between the scanner's X-ray source and detector array. When the imaging region of the patient's body is located in the FOV, the X-ray source is operable to provide X-rays that pass through the imaging region and are incident on the detectors. The patient is usually supported lying on a couch that is moveable axially along an axis, conventionally the "z-axis" of a Cartesian coordinate system, relative to the gantry to position and move the patient axially through the FOV. The X-ray source is rotatable around the z-axis. The size and location of the FOV is defined by a largest circle in a plane perpendicular to the z-axis that has its center on the z-axis and for which trajectories of X-rays from the X-ray source that are detectable by the detector array are substantially tangent to the circle. For convenience of presentation and visualization a circularly cylindrical region within the X-ray beam having its axis coincident with the z-axis and a cross section coincident with the largest circle is referred to as a CT scanner's FOV.

In many multislice CT scanners the detectors in the detector array are generally configured in rows and columns of detectors positioned on a circularly cylindrical surface having an axis that is parallel to the z-axis and passes through the X-ray source focal spot. Conventionally, the columns are parallel to the z-axis and the rows lie along arcs of circles that are perpendicular to the z-axis. Features of the cone beam and detector array are conveniently located with respect to a sagittal plane and a transverse plane. The sagittal plane is a plane that contains the z-axis and passes through the X-ray source focal spot. The transverse plane is a plane that passes through the X-ray source focal spot and is perpendicular to the z-axis. A location of a given column is conveniently defined by an azimuth angle. The azimuth angle is an angle that a plane containing the column and passing through the focal spot makes with the sagittal plane. A given row is conveniently located by a declination angle. A declination angle is an angle that a plane containing the row and passing through the focal spot makes with the transverse plane. The dimensions of the cone beam and detector array are generally matched so that X-rays from the X-ray source are substantially confined within a solid angle subtended by the detector array at the focal spot.

To image features and organs in an imaging region of a patient, the couch supporting the patient is moved relative to the gantry along the z-axis to translate the patient's imaging region through the scanner's FOV. As the imaging region moves through the FOV the X-ray source is rotated around the z-axis to illuminate thin "slices" of the imaging region that are substantially perpendicular to the z-axis with X-rays at a plurality of different view angles. At each view angle and different axial positions along the z-axis of the imaging region, detectors in the array of detectors measure intensity of X-rays from the X-ray source that pass through slices of the imaging region. The intensity of X-rays measured by a given detector in the array of detectors is a function of an amount by which X-rays are attenuated by material in a slice of the imaging region along a path length, hereinafter "attenuation path", from the X-ray source, through the imaging region slice to the given detector. The measurement provides information on composition and density of tissue in the imaging region slice along the attenuation path.

In some CT scanners an axial scan of a patient is performed in which the patient is moved stepwise along the z-axis to "step" the imaging region through the FOV. Following each step, the X-ray source is rotated through 360 degrees or about 180 degrees to acquire attenuation measurements for slices in the imaging region. In some CT scanners a "spiral scan" of a patient is performed in which the patient is steadily translated through the gantry while the X-ray source simultaneously rotates around the patient and attenuation measurements for slices in the region are acquired "on the fly".

The attenuation measurements for slices of an imaging region of a patient provided by the detectors in an axial or spiral scan are generally processed using CT reconstruction algorithms known in the art as filtered back projection algorithms to map the absorption coefficient of the imaging region as a function of position. The map is used to display and identify internal organs and features of the imaging region.

CT image reconstruction algorithms are used to process attenuation data assuming that for each slice in the imaging region and for each voxel of the slice, attenuation data is acquired for each view angle for an attenuation path that passes through the voxel. To satisfy this assumption the FOV of a CT scanner used to image a patient's imaging region is generally configured sufficiently large to encompass the full width of the patient's body at the imaging region. If portions of an imaging region of a patient cannot fit inside the FOV for all view angles, attenuation data is generally incomplete and artifacts may be generated in images reconstructed from the data. As a result, detector arrays of conventional CT scanners are relatively large and comprise relatively large numbers of detectors.

Typically, a row of detectors in a multislice CT scanner detector array has between 700-1,000 detectors and there may be as many as 64 rows of detectors in the array so that a detector array in a typical CT scanner may have as many as 64,000 X-ray detectors. Future CT scanners are expected to have even larger numbers of detectors. The large number of detectors requires an extensive electronic support infrastructure for signal processing and data transfer. The detectors also require complicated mechanical support systems that are configured to high tolerances that provide in addition to mechanical support, various other functions such as radiation collimation and shielding for electronics associated with the detectors. As a result, CT scanning systems are relatively complicated and expensive.

CT scanning can involve exposing a large part of a patient's body to potentially damaging X-ray radiation. Damage from exposure to X-ray radiation is thought to be cumulative and for safety and health reasons it is desirable to minimize a patient's exposure to X-ray radiation during a CT scan. For some applications for which a region of interest in a patient's body is a relatively localized region inside an imaging region it is possible to limit radiation by limiting radiation exposure to parts of the body that are outside of the localized region of interest. For example, U.S. Pat. No. 6,385,278, the disclosure of which is incorporated herein by reference, provides a method of reducing exposure of a patient to X-rays during a CT scan when a region of interest to be imaged in a patient's body is a relatively small region, such as the heart. The patent describes collimating the beam so that tissue in the patient's body outside the heart receives less radiation than heart tissue.

SUMMARY OF THE INVENTION

An aspect of some embodiments of the present invention relates to providing a CT scanner having a FOV sufficient to encompass the width of a patient's body that is simpler and relatively inexpensive to produce in comparison with prior art CT scanners, yet provides CT images having image quality satisfactory for medical applications.

In accordance with an aspect of some embodiments of the invention, the CT scanner comprises an array of X-ray detectors comprising at least one relatively high resolution region and at least one relatively low resolution region.

The at least one high resolution region comprises X-ray detectors that are relatively densely packed per unit area of the region and are separated one from the other substantially only by thin septa that function to reduce cross talk between adjacent detectors and optionally by anti-scatter shielding that collimates X-rays. The at least one low resolution region comprises detectors having a relatively low packing density per unit area of the region. In some embodiments of the invention the low density of the low resolution region is provided, at least in part by configuring X-ray detectors so that they are separated one from the other by "dead" areas insensitive to X-rays that are substantially larger than dead areas generated by septa typically used in CT scanners. Optionally, X-ray detectors in the low resolution regions are separated by dead areas having areas equal to or greater than a size of the X-ray detectors. In some embodiments of the invention, the low density is provided, at least in part, by configuring the detector array so that at least some X-ray detectors at relatively large absolute value azimuth angles are larger than detectors at smaller absolute value azimuth angles. Optionally at least some of the relatively large detectors at large absolute value azimuth angles are separated by "typical" septa.

Optionally, the at least one high resolution region comprises a single "central" high resolution region having columns of detectors located at relatively small absolute value azimuth angles flanked on at least one side by a low resolution "wing" region. Optionally, the central high resolution region is flanked on both sides by low resolution wing regions.

In some embodiments of the invention, the wings on either side of the central high resolution region have a same area. Optionally, the wings are mirror images of each other. Optionally, areas that are dead areas in one of the wings are homologous to areas of the other wing that comprise an X-ray detector. Optionally, all the detectors in the detector array have a same size. Optionally, detectors in the detector array have different sizes. For example, detectors in low detector density regions of the detector array may be larger than detectors in high density regions of the detector array.

The central high resolution region of the detector array provides higher resolution attenuation data for a portion of a patient's imaging region that is illuminated with X-rays that are incident on detectors in the central region than for a portion that is illuminated with X-rays incident on detectors in the wings. The portion of the imaging region for which higher resolution attenuation data is acquired passes through a central cylindrical region, hereinafter a high resolution FOV (HR-FOV), of the scanner's FOV when the patient is scanned. The cylindrical region of the HR-FOV is concentric with the cylindrical region that demarks the FOV. A region of the FOV between the central high resolution HR-FOV and the outer boundary of the FOV is referred to as a "low resolution FOV" (LR-FOV).

To provide a set of attenuation data suitable for processing in accordance with various back projection algorithms to image the imaging region, data provided by detectors in the wings, i.e. data acquired from the LR-FOV, is processed, optionally by normalization and interpolation, to generate approximations to attenuation data that would be expected were the wings to have a resolution the same as the resolution of the high resolution region. The processed low resolution data is combined with the high resolution data to provide the complete attenuation data set. The inventors expect that the complete data set can be processed to provide an image of a localized region of interest (LROI) in a patient's body that passes through the HR-FOV that has a resolution satisfactory for many medical applications. For example, the heart, spine or liver of a patient may be imaged with satisfactory resolution using a CT scanner in accordance with an embodiment of the invention.

In accordance with an aspect of some embodiments of the invention the couch of the CT scanner is translatable horizontally and/or vertically to center a localized region of interest in a patient's body in the HR-FOV.

In accordance with an aspect of some embodiments of the invention, the X-ray source of the CT scanner is collimated so that X-rays from the source illuminate substantially only those regions of the detector array that are sensitive to X-rays. The collimating shielding results in a substantial decrease in exposure of a patient to X-rays during a CT-scan.

In some embodiment of the invention, shielding is used to decreases intensity of X-rays from the X-ray source that illuminate the at least one low resolution region of the detector array. For example, for a detector array having a high resolution region flanked by two low resolution wings, a "butterfly filter" having a smoothly varying thickness that increases with azimuth angle may be used to attenuate X-rays that illuminate the wings. Optionally, uniform thickness "plate filters" may be used to attenuate X-rays that illuminate the wings.

As a result of the configuration of detectors in an X-ray detector array in accordance with an embodiment of the invention, a number of detectors in the array is substantially reduced in comparison to prior art CT scanners having a same FOV. A CT scanner in accordance with an embodiment of the invention therefore requires less intricate and complicated mechanical and electronic support structures and may be produced relatively inexpensively. It is expected that CT scanners in accordance with embodiments of the invention will be affordable by a larger number of medical centers than the number of medical centers that can afford prior art CT scanners. It is also expected that individual medical centers will be able to afford a greater number of CT scanners in accordance with an embodiment of the invention than a number of prior art CT scanners that they can afford. CT scanners in accordance with an embodiment of the present invention are therefore expected to make the benefits of CT scanning available to an increased population of patients. In addition, the benefits will be able to be provided at a lower dose of radiation exposure to patients.

There is therefore provided in accordance with an embodiment of the invention, A CT scanner comprising: a rotor rotatable about an axis of rotation; an X-ray source mounted to the rotor having a focal spot from which an X-ray beam emanates; an X-ray detector array comprising a plurality of X-ray detectors for detecting X-rays in the X-ray beam; wherein the detector array has at least one high resolution region in which detectors have a high packing density and at least one low resolution region in which detectors have a low packing density and are separated by X-ray insensitive regions substantially larger than insensitive regions resulting from septa between detectors that function to reduce detector cross talk.

In some embodiments of the invention, the at least one high resolution region comprises a single high resolution region. Optionally, the high resolution region is flanked on one side by a single low resolution area.

In some embodiments of the invention, the high resolution region is flanked on both sides by a low resolution region. Optionally, the low resolution regions have a same size. Optionally, the detectors in the low resolution regions are arrayed in mirror image configurations.

In some embodiments of the invention, the detectors in the low resolution regions are arrayed so that areas of one of the low resolution regions that have detectors are homologous with areas of the other low resolution region that do not have detectors.

In some embodiments of the invention, adjacent detectors in a low resolution region of the detector array are separated by a distance greater than 0.3 mm. In some embodiments of the invention, adjacent detectors in a low resolution region of the detector array are separated by insensitive regions having areas greater than or equal to about the size of the X-ray detectors.

There is further provided in accordance with an embodiment of the invention a CT scanner comprising: a rotor rotatable about an axis of rotation; an X-ray source mounted to the rotor having a focal spot from which an X-ray beam emanates; an X-ray detector array comprising a plurality of X-ray detectors for detecting X-rays in the X-ray beam having at least one high resolution region in which detectors have a high packing density and at least one low resolution region in which detectors have a low packing density; wherein size of the detectors is a function of distance from a sagittal plane that passes through the focal spot and axis of rotation. Optionally, detectors farther from the sagittal plane are larger than detectors closer to the plane.

In some embodiments of the invention, the X-ray source and detector array define a field of view (FOV) for the scanner having a high resolution portion and a low resolution portion, wherein relatively high resolution attenuation data is acquired for a region of a patient imaged by the CT scanner that passes through the high resolution portion and relatively low resolution attenuation data is acquired for a region of the patient that passes through the low resolution region of the FOV.

Optionally, the high resolution region is defined by an area within a first circle having a first diameter and the low resolution portion is defined by an area between the first circle and a second circle having a second diameter that is concentric with the first circle. Optionally, the first circle has a diameter less than or equal to about 25 cm. In some embodiments of the invention, the second circle has a diameter less than or equal to about 50 cm.

In some embodiments of the invention, the scanner comprises an X-ray radiation shielding that attenuates X-rays provided by the X-ray source. Optionally, the radiation shielding attenuates X-rays that illuminate the at least one low density region. Additionally or alternatively the radiation shielding optionally comprises plates of absorbing material having substantially uniform thickness. In some embodiments of the invention, the shielding comprises shielding having a smoothly varying thickness that increases with displacement to either side of a sagittal plane that passes through the focal spot and axis of rotation. Optionally, the shielding is a "butterfly filter". In some embodiments of the invention, the CT scanner comprises X-ray radiation shielding that collimates X-rays from the X-ray source so that insensitive areas of the detector array are substantially not illuminated by X-rays.

In some embodiments of the invention, the CT scanner comprises a processor that processes attenuation data acquired with the detector array and calibrates data acquired responsive to X-rays attenuated by the shielding to data acquired responsive to X-rays that are not attenuated by the shielding.

In some embodiments of the invention, the CT scanner comprises a processor that processes data for a region of a body imaged by the scanner acquired by the low resolution detector region to estimate data that would be acquired for the body region were the low resolution detector region to have a resolution substantially equal to that of the high resolution detector region. Optionally, the data acquired by the low resolution data is processed using an interpolation algorithm.

In some embodiments of the invention, the detectors are arrayed in rows and columns In some embodiments of the invention, the CT scanner is a single slice scanner. In some embodiments of the invention, the CT scanner is a multislice scanner.

BRIEF DESCRIPTION OF FIGURES

Non-limiting examples of embodiments of the present invention are described below with reference to figures attached hereto. In the figures, identical structures, elements or parts that appear in more than one figure are generally labeled with a same numeral in all the figures in which they appear. Dimensions of components and features shown in the figures are chosen for convenience and clarity of presentation and are not necessarily shown to scale. The figures are listed below.

DETAILED DESCRIPTION OF EXEMPLARY EMBODIMENTS

Figure 1:
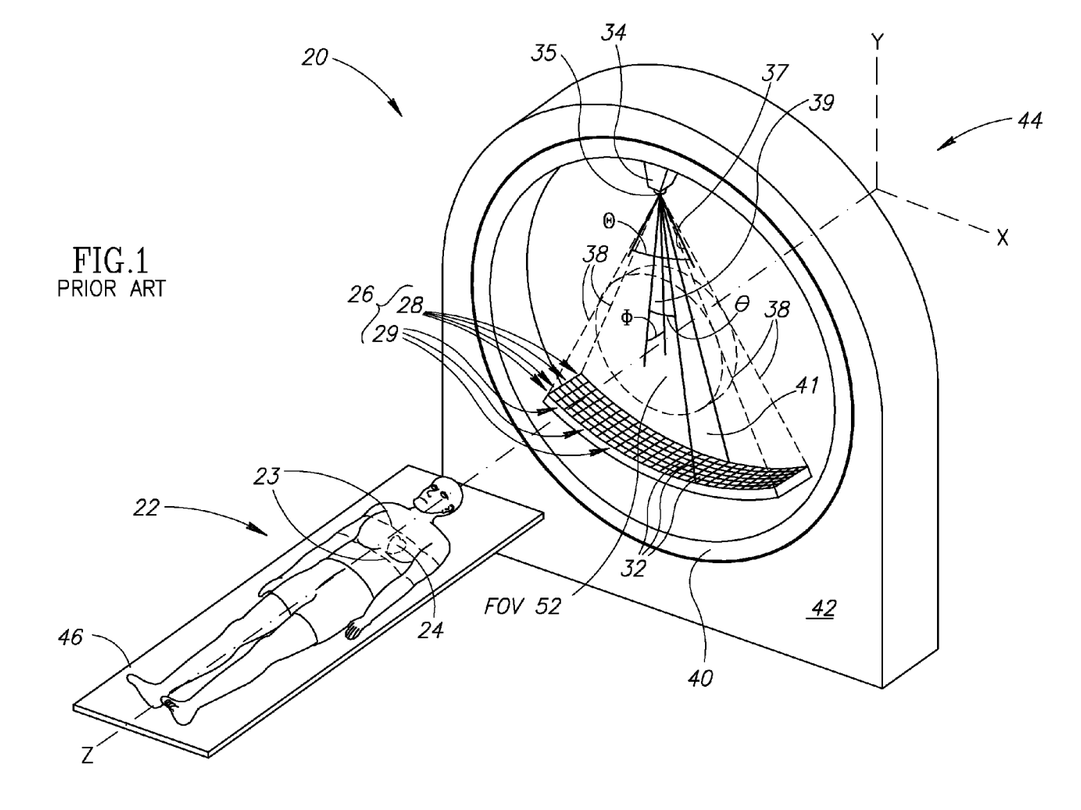
FIG. 1 schematically shows a multislice CT scanner for imaging patients, in accordance with prior art.

FIG. 1 schematically shows a multislice CT scanner 20 for imaging patients, in accordance with prior art. In FIG. 1 a patient 22 having an imaging region indicated by dashed lines 23 and a localized region of interest LROI 24 within the imaging region shown in dashed lines is to be imaged with scanner 20. LROI 24 is by way of example, the patient's heart. Only features of multislice scanner 20 germane to the discussion of the present invention are shown in FIG. 1.

Multislice scanner 20 comprises a detector array 26 of X-ray detectors 32 and an X-ray source 34 that provides a cone beam of X-rays shown in dashed lines 38 for illuminating patient 22 with X-rays. Cone beam 38 emanates from a focal spot 35 of X-ray source 34. X-ray source 34 and detector array 26 are mounted to a rotor 40 of a gantry 42. Rotor 40 is rotatable around the z-axis of a coordinate system 44.

Detectors 32 in detector array 26 are configured in rows 28 and columns 29 of detectors 32 so that each detector 32 substantially faces focal spot 35 of X-ray detector 34. Columns 29 are parallel to the z-axis and detector rows 28 are arcs of circles having their centers located substantially at focal spot 35 and their planes substantially perpendicular to the z-axis. By way of example, and for convenience of presentation, detector array 26 is schematically shown comprising a relatively small number of rows and columns 28 and 29 of detectors 32 and a relatively small number of the detectors. A modern multislice CT scanner may, by way of example, comprise as many as 64 rows and 1000 columns of detectors 32 and many tens of thousands of X-ray detectors 32 and CT scanners and even larger numbers of X-ray detectors are possible.

Cone beam 38 has a fan shaped cross section in a transverse plane 37 that passes through focal spot 35 and is perpendicular to the z-axis. An opening angle $\Theta$ of the fan shaped cross section is referred to as the fan angle of cone beam 38. The cone beam has an angular extent $\Phi$ in a sagittal plane 39 that contains the z-axis and passes through focal spot 35. Cone beam 38 and detector array 26 are matched so that X-rays in the cone beam illuminate substantially all and substantially only detector array 26.

A location of a given column 29 of detectors in array 26 is indicated by an azimuth angle θ that a plane containing the column and passing through focal spot 35 makes with sagittal plane 39. An azimuth angle θ for and a plane 41 that together with sagittal plane 39 defines the azimuth angle for one of rows 29 is shown in FIG. 1. Let counterclockwise and clockwise azimuth angles, as seen looking along the z-axis to the origin of coordinate system 44, be respectively positive and negative azimuth angles. Then extreme detector columns 29 at opposite ends of array 26 are usually located at azimuth angles equal to +$\Theta$/2 and −$\Theta$/2. (For simplicity it is assumed that cone beam 38 is symmetric relative to transverse plane 37 and sagittal plane 39, although asymmetric beam configurations can be used on CT scanners as well). Similarly, let position of a given detector row 28 be indicated by a declination angle φ relative to transverse plane 37 and counterclockwise and clockwise declination angles as seen looking along the positive x-axis to the origin of coordinate system 44 be positive and negative declination angles respectively. The extreme rows 28 of detectors 32 are usually located at declination angles φ equal to +$\Phi$/2 and −$\Phi$/2.

A field of view 52, i.e. FOV 52, of scanner 20 is located between X-ray source 34 and detector array 26 and is indicated by dashed lines. Field of view 52 is a substantially cylindrical region having an axis coincident with the z-axis and size determined by fan and cone beam angles $\Theta$ and $\Phi$ and distance of focal spot 35 from the z-axis. FOV 52 is large enough so that width of patient 22 is fully contained within the FOV and the FOV typically has a diameter equal to about 50 cm. Patient 22 is supported on a couch 46 during imaging of the patient. Couch 46 is controllable to be translated axially along the z-axis to move patient 22 and imaging region 23 through FOV 52. A controller (not shown) controls motion of couch 46, rotor 40 and intensity of X-rays provided by X-ray source 34.

Multislice scanner 20 can generally be operated in an axial mode or in a helical mode to image imaging region 23 of patient 22. In an axial mode controller 48 controls motion of couch 46 to step patient 22 along the z-axis and move imaging region 23 through FOV 52 of scanner 20. Following each step, rotor 40 rotates around the z-axis to rotate detector array 26, X-ray source 34 and its cone beam 38 around patient 22 so as to acquire attenuation measurements of imaging region 23 from a plurality of view angles. In a helical mode, patient 22 is moved continuously along the z-axis through FOV 52 as rotor 40 simultaneously, continuously rotates around the z-axis to acquire attenuation measurements of imaging region 23 at different view angles. In FIG. 1 X-ray source 34 and detector array 26 are shown oriented along the vertical at a view angle optionally referred to as a 0° view angle.

Attenuation data acquired for imaging region 23 is processed using any of various back projection algorithms to provide an image of internal tissue and organs in imaging region 23 and in particular an image of localized region of interest LROI 24, i.e. the heart, of patient 22. It is noted that to acquire the image of the heart, detector array 26 is completely filled with detectors 32 and is used to acquire substantially same resolution data for the entire volume of imaging region 23.

Figure 2A:
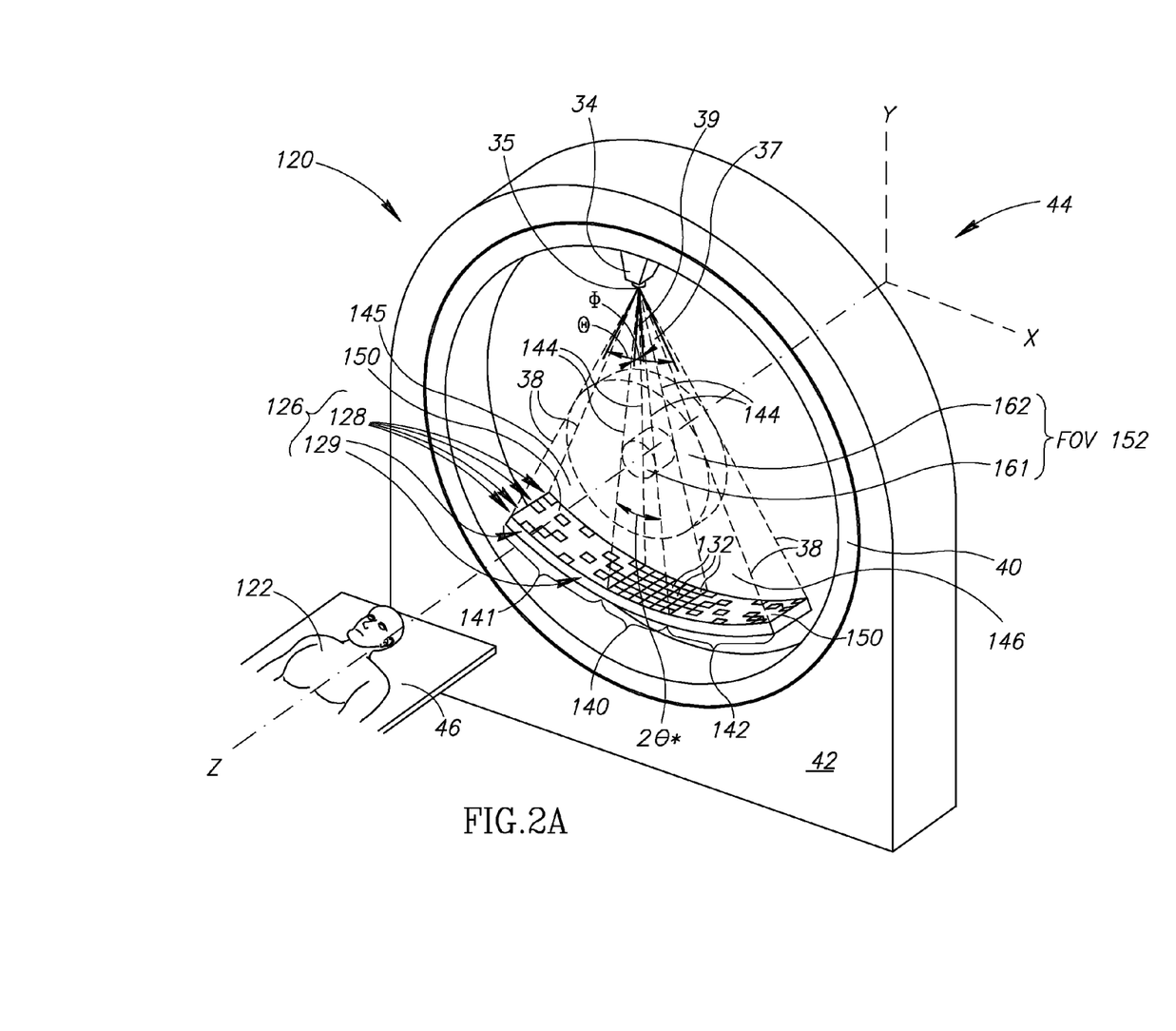
FIG. 2A schematically shows a multislice CT scanner for imaging patients, in accordance with an embodiment of the present invention.

FIG. 2A schematically shows a multislice CT scanner 120 and patient 122 (partially shown) who is to be imaged using the scanner, in accordance with an embodiment of the present invention.

Figure 2B:
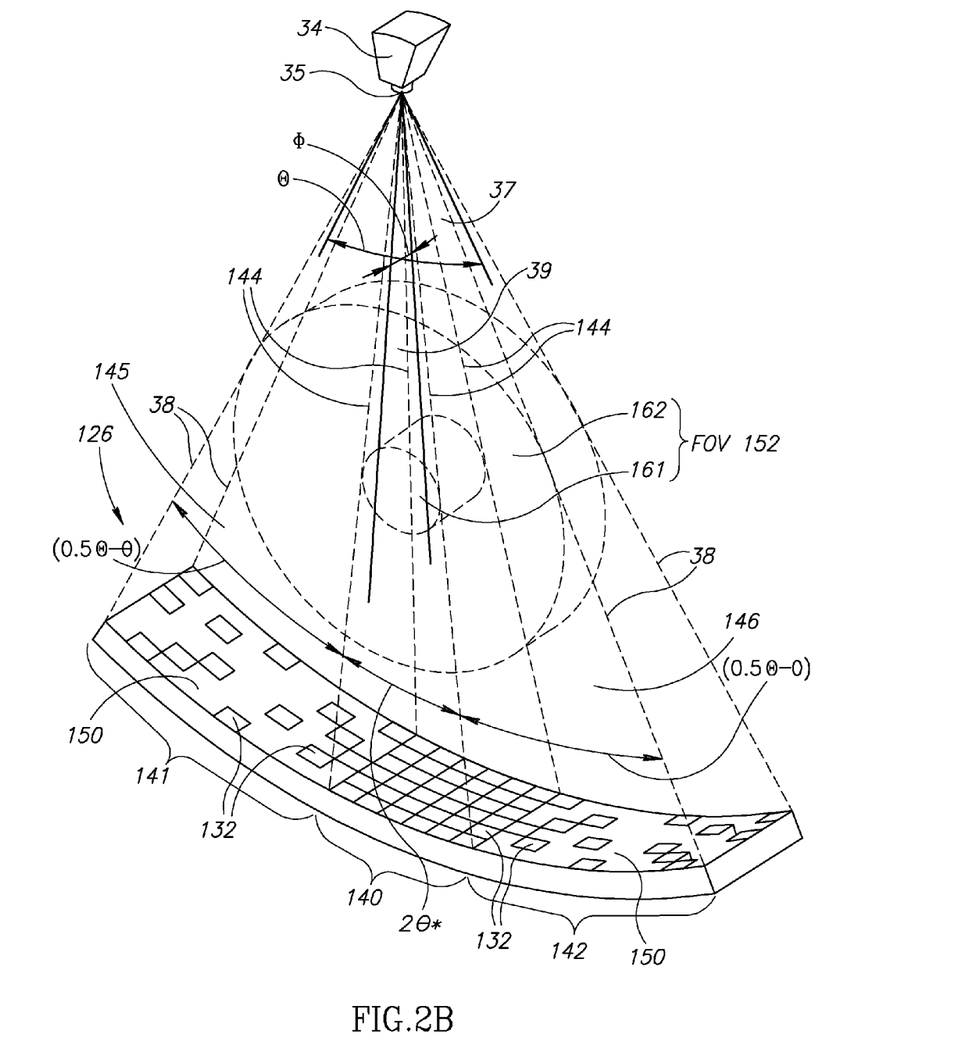
FIG. 2B schematically shows an enlarged view of the detector array and cone beam of the CT scanner shown in FIG. 2A, in accordance with an embodiment of the invention.

Multislice CT scanner 120 comprises many of the components and features of CT scanner 20 shown in FIG. 1 and is assumed to have a cone beam 38 having a fan angle $\Theta$ and cone angle $\Phi$ and an FOV 152 having a same size as FOV 52 of CT scanner 20. However, CT scanner 120 comprises an array 126 of rows 128 and columns 129 of X-ray detectors 132 having high and low resolution regions that generate internal structure in FOV 152 that is absent in prior art FOV 52. FIG. 2B schematically shows part of scanner 120 enlarged for convenience of presentation of details of cone beam 38 and detector array 126.

In accordance with an embodiment of the invention, detector array 126 comprises a central high resolution region 140 having a relatively high packing density of X-ray detectors 132 and optionally two low resolution wing regions 141 and 142 for which packing density of the X-ray detectors is relatively low.

Any of various conventional spatial configurations of X-ray detectors and detector sizes may be used to configure detectors 132 in detector array 126. Optionally, central region 140 is symmetric with respect to sagittal plane 39 and is bounded by detector rows 132 having azimuthal angular positions θ* and −θ*. A central portion of cone beam 38 indicated by dashed lines 144 that illuminates central region 140 therefore has an azimuthal extent, i.e. a fan angle, equal to 2θ*. Side portions 145 and 146 of cone beam 38 illuminate wings 141 and 142 respectively of detector array 126. Side portions 145 and 146 span azimuth angles from θ* to 0.5Θ and −θ* to −0.5Θ respectively and have azimuthal extents equal to (0.5Θ−θ*) (FIG. 2B). Various different spatial distributions of X-ray detectors and detector sizes may be used to configure X-ray detectors in "sparsely populated" wings 141 and 142 of detector array 126. In accordance with an embodiment of the invention, detectors 132 in wings 141 and 142 are separated by relatively large dead areas 150 that are insensitive to X-rays. The dead areas are substantially larger than dead areas generated by septa typically used in CT scanners to separate detectors in a CT scanner detector array and reduce cross talk. Septa including optional anti-scattering shielding foils typically have thickness in a range from about 0.05 millimeters to about 0.3 millimeters.

Optionally, X-ray detectors in wings 141 and 142 are separated by dead areas having areas equal to or greater than a size of the X-ray detectors. Optionally X-ray detectors in wings 141 and 142 are separated by a distance equal to or greater than 0.25 of a largest dimension that characterizes a sensitive area of an X-ray detector in the array. Optionally the detectors are separated by a distance equal to or greater than 0.5 of a largest dimension that characterizes a sensitive area of an X-ray detector in the array. Optionally the detectors are separated by a distance equal to or greater than 0.75 of a largest dimension that characterizes a sensitive area of an X-ray detector in the array. By way of example, all detectors 132 in detector array 126 have a same size.

Optionally, the respective configurations of X-ray detectors in wings 141 and 142 are mirror images of each other. Optionally, configurations of X-ray detectors in wings 141 and 142 are such that regions of one of the wings that have detectors are homologous with regions of the other wing that do not have detectors. "Complimentary" wing configurations for which homologous regions are "negatives" of each other can be advantageous. For a same total number of X-ray detectors "negative" detector configurations can provide data from more regions of an imaging region than mirror image detector configurations.

Whereas detectors 132 in central region 140 and wings 141 and 142 are schematically shown as having a same size and shape, detectors in different regions of detector array 126 may have different sizes and/or shapes. For example, detectors 132 in wing regions 141 and 142 may be larger or smaller than detectors in central region 140. Nor do detectors in a same region, such as a wing 141 or 142 have to have a same size and/or shape. In addition, detectors 132 in wings 141 and 142 do not necessarily lie in rows defined by rows 128 of detectors 132 in central region 140.

Figure 2C:
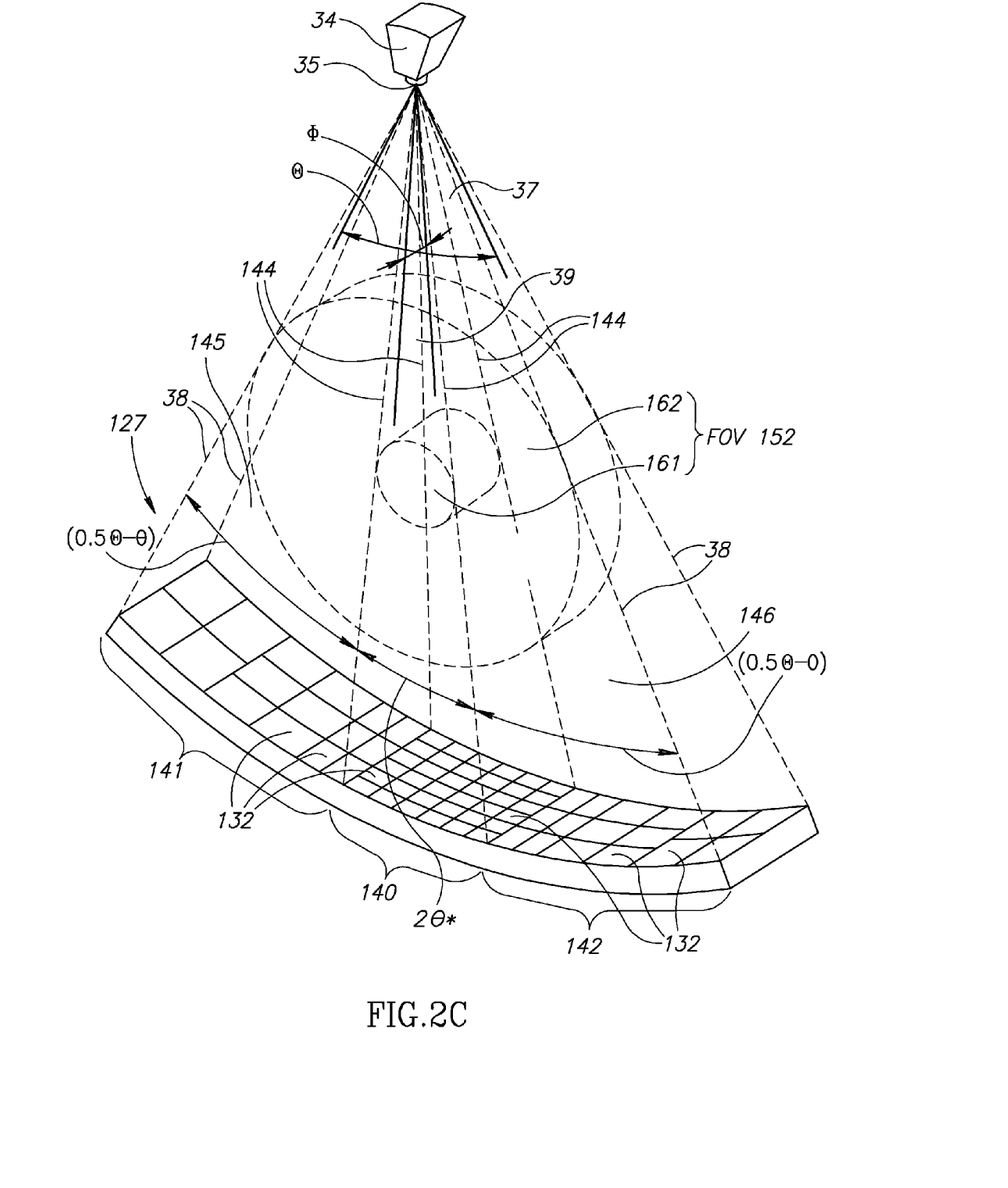
FIG. 2C schematically shows an enlarged view of another detector array, in accordance with an embodiment of the invention.

FIG. 2C schematically shows a detector array 127 in accordance with an embodiment of the invention having a configuration of detectors 132 different from that shown in FIGS. 2A and 2B. Detectors 132 in low resolution wing regions 141 and 142 are substantially contiguous with each other except for septa but are substantially larger than detectors 132 in central high resolution region 140. The relative low detector density in wings 141 and 142 is achieved as a result of the relative large size of detectors 132 in the wing regions. In array 127 by way of example, detector size in wings 141 and 142 increase with increase in the absolute value of the azimuth angle of detectors in the wings, i.e. as distance of the detectors from central detector region 140 increases.

It is noted that whereas in the above discussion, detector arrays 126 and 127 (FIGS. 2B and 2C respectively) are symmetric and have two wings 141 and 142 a CT scanner in accordance with an embodiment of the invention may have an asymmetric cone beam and/or detector array. For example, a CT scanner in accordance with an embodiment of the invention may have a detector array comprising central region 140 but only one of wings 141 and 142 and a cone beam shielded to match the shape of the asymmetric detector array. It is also noted that whereas in the above discussion detector arrays 126 and 127 are assumed to lie on a continuous, circularly cylindrical surface, detector arrays, in accordance with an embodiment of the invention may be formed using any of various techniques and methods known in the art and are not limited to circularly cylindrical arrays. For example, a detector array in accordance with an embodiment of the invention may be configured using at least one flat panel array.

Central region 140 of detector array 126 and its corresponding central portion 144 of cone beam 38 define a high resolution region HR-FOV 161 of FOV 152. Side regions 141 and 142 of detector array 126 and corresponding side portions 145 and 146 of cone beam 38 define a low resolution region LR-FOV 162 of FOV 152. Absorption of X-rays is sampled at a higher resolution for a portion, hereinafter referred to as a "core", of an imaging region of a patient that passes through HR-FOV 161 during a scan of the patient than for a portion, hereinafter a "periphery", of the imaging region that passes through LR-FOV 162.

In an embodiment of the invention, cone beam 38 and detector array 126 are configured so that FOV 152 has a diameter sufficient to encompass a typical width of a patient imaged with CT scanner 120 and HR-FOV 161 has a diameter sufficient to encompass local regions of interest, i.e. LROIs, such as the spine, heart or liver, within the patient's body. For example, FOV 152 may have a diameter of about 50 cm and HR-FOV 161 a diameter of about 25 cm. Other diameters for FOV 152 and HR-FOV 161 are possible and can be advantageous. For example, in a children's clinic the FOV and HR-FOV of a CT scanner in accordance with an embodiment of the invention may have dimensions that are smaller than those noted above.

In accordance with an embodiment of the invention, the relatively sparsely sampled data acquired for the low resolution periphery is interpolated to approximate data that would have been collected for the periphery by X-ray detectors present in dead regions 150 of detector array 126. A "combined" data set of attenuation data comprising high resolution data acquired from HR-FOV 161 for the core of the imaging region and interpolated low resolution data acquired from LR-FOV 162 for the periphery of the imaging region is processed to provide an image of the imaging region and in particular an image of the core.

It is noted that for CT scanners in accordance with an embodiment of the invention, having only one detector wing, i.e. wing 141 or wing 142, data collected by the one wing for the periphery at a given view angle can be used to complete data acquired for the periphery at a view angle equal to the given angle plus 180°. Similarly, for CT scanners in accordance with an embodiment of the invention, having complimentary wing configuration, i.e. wing configurations for which homologous areas are "negatives" of each other, data collected at a given view angle for the periphery may be used to complete data acquired for the periphery at a view angle equal to the given angle plus 180°.

The inventor expects that an image of the core region can be generated from the combined data set with a relatively small or negligent degradation of image quality relative to quality of an image realized from a data set comprising high resolution data for both the core and the periphery. In this regard, the inventor notes that CT images acquired using a CT scanner with part of the scanner's X-ray beam shielded to reduce patient exposure to X-rays acquires relatively high resolution attenuation data for part of an imaging region of a patient and relatively low resolution attenuation data for a remainder of the imaging region. U.S. Pat. No. 6,385,278 referenced above describes generating a CT image of a patient's heart from data acquired using an X-ray beam shielded to reduce patient X-ray exposure. The data comprises high resolution attenuation data acquired for the heart region from an unshielded portion of the beam and data interpolated from low resolution attenuation data acquired for tissue outside of the heart region from shielded portions of the beam. The patent reports that the image of the heart has a resolution that approximates that of an image produced from attenuation data comprising only high resolution data.

Often, a particular local region of interest LROI, for example the heart or liver, of a patient to be imaged by a CT scanner such as CT scanner 120, in accordance with an embodiment of the invention, is not intersected by or located near to the patient's sagittal plane. Were the patient to be scanned with scanner 120 and translated through FOV 152 without properly aligning the patient with respect to high resolution HR-FOV 161 of the FOV, the LROI would not necessarily be completely included in a core region of the patient imaged with data from HR-FOV 161. All the LROI volume might not pass through HR-FOV and a portion would pass through LR-FOV 162. Therefore, in accordance with an embodiment of the invention, couch 46 in CT scanner 120 is moveable along the x and y directions so that during translation of the patient through FOV 152 a desired LROI may be centered in HR-FOV 161.

Figure 3A:
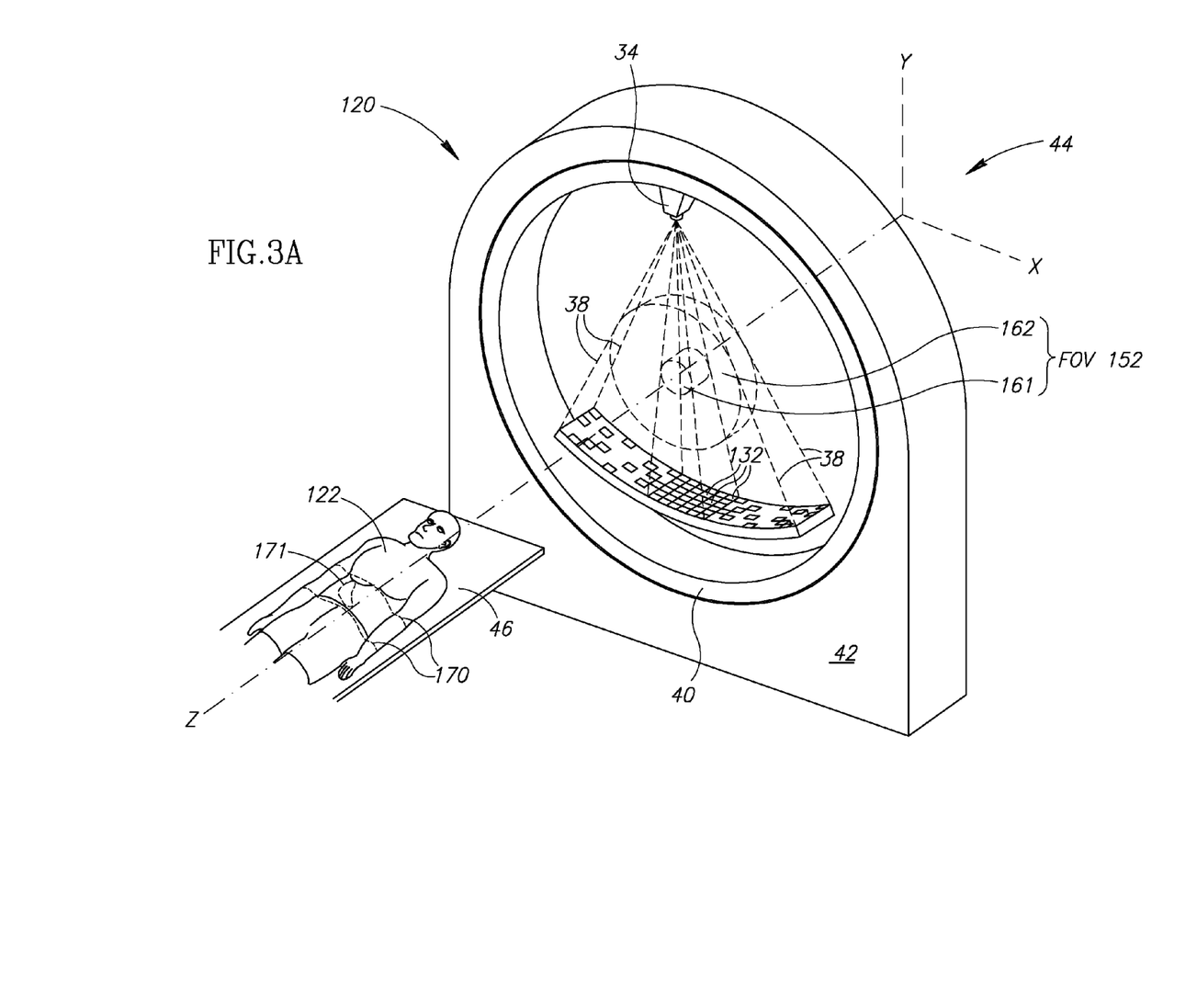
FIGS. 3A and 3B schematically show a patient being imaged with a CT scanner, in accordance with an embodiment of the invention.
Figure 3B:
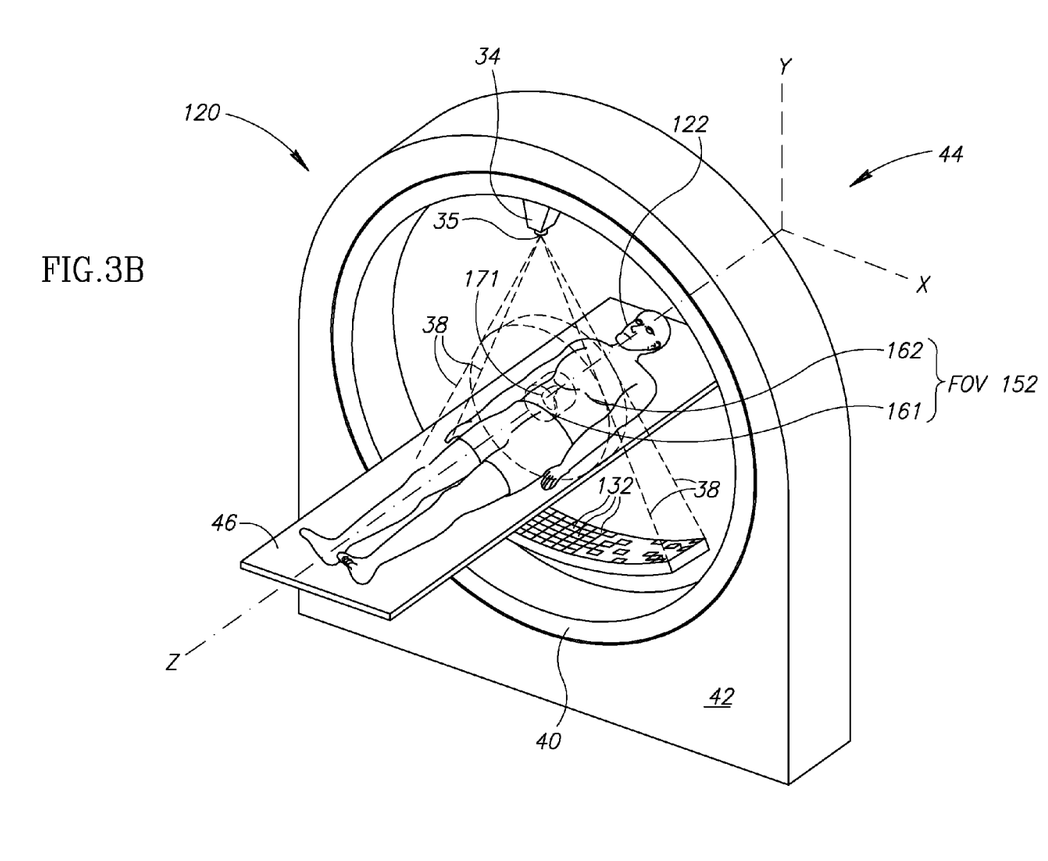

FIGS. 3A and 3B schematically shows patent 122 being imaged by CT scanner 120, in accordance with an embodiment of the invention. By way of example, in FIG. 3A an imaging region of patient 122 is an abdominal region indicated by dashed lines 170 and an LROI of the patient is the patient's liver 171. In FIG. 3A patient 122 is schematically shown before being aligned with the z-axis and the patient's liver is displaced from the z-axis along the negative x-axis. Were patient 122 to be translated through FOV 152 without aligning the patient's liver with the z-axis, a portion of the liver might not be imaged in high resolution HR-FOV 161 of FOV 152 and an image of the liver might not have desirable resolution.

In accordance with an embodiment of the invention, the controller (not shown) of CT scanner 120 adjusts the position of couch 46 so that liver 171 is substantially centered on the z-axis before and during translation of patient 122 through FOV 152. As a result, during scanning of patient 122 with the scanner when imaging region 170 of the patient passes through FOV 152, the liver is completely within HR-FOV 161 and high resolution data is acquired for the liver. FIG. 3B schematically shows patient 22 passing through FOV 152 and the patient's liver centered in HR-FOV 161.

In accordance with an embodiment of the invention, to reduce exposure of a patient to X-rays during scanning with a CT scanner in accordance with an embodiment of the invention, the scanner's cone beam is shielded to collimate X-rays from the beam so that X-rays are provided substantially only along directions that are incident on X-ray sensitive areas of detector array 126.

Figure 4A:
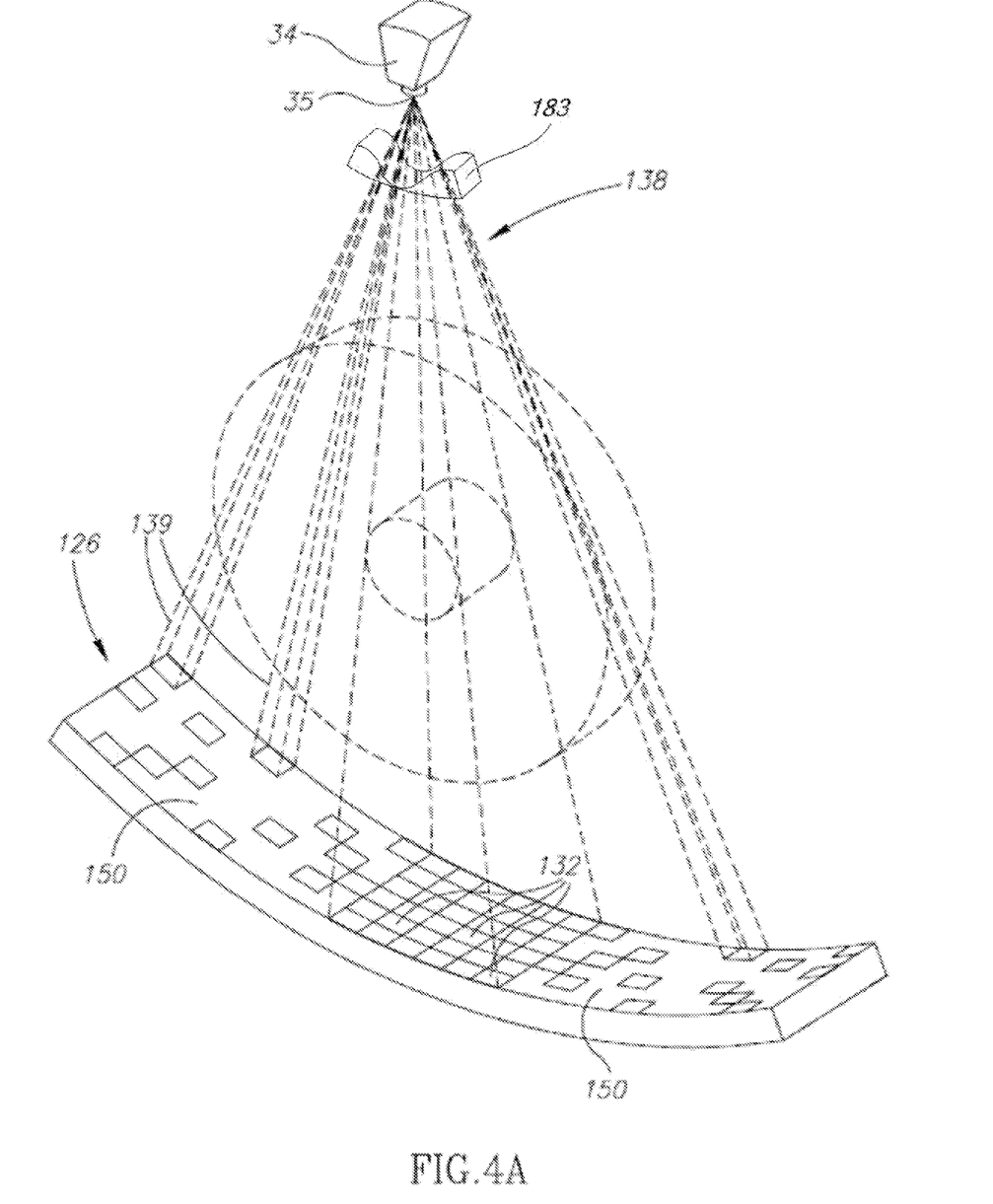
FIGS. 4A and 4B schematically show an X-ray cone beam shielded to reduce X-ray exposure of a patient during imaging, in accordance with an embodiment of the invention.

FIG. 4A schematically shows X-ray source 34 comprising shielding (not shown) to provide a collimated X-ray cone beam 138 suitable for use with detector array 126 in accordance with an embodiment of the invention. As a result of the collimation, cone beam 138 illuminates substantially only detectors 132 in detector array 126 with X-rays and dead areas 150 are not exposed to X-rays. Regions 139 of collimated cone beam 38 that provide X-rays that illuminate detectors 132 in array 126 are indicated for some detectors 132.

X-ray shielding configurations different from that used to provide cone beam 138 may be used, in accordance with an embodiment of the invention to reduce a patient's exposure to X-rays. For example, shielding may be configured to shield and reduce X-ray intensity in a portion or portions of a cone beam that illuminate a wing or wings of a detector array, such as detector array 126 (FIG. 2A-FIG. 4) while, optionally, not affecting a portion of the X-ray beam that illuminates the high resolution region 140 of the detector array. The shielding may by way of example take a form of a radiation filter 183, conventionally referred to as a "butterfly filter", having a smoothly varying thickness that increases with displacement to either side of focal spot 35. By way of another example uniform thickness "plate filters" may be used to attenuate X-rays that illuminate the wings.

Figure 4B:
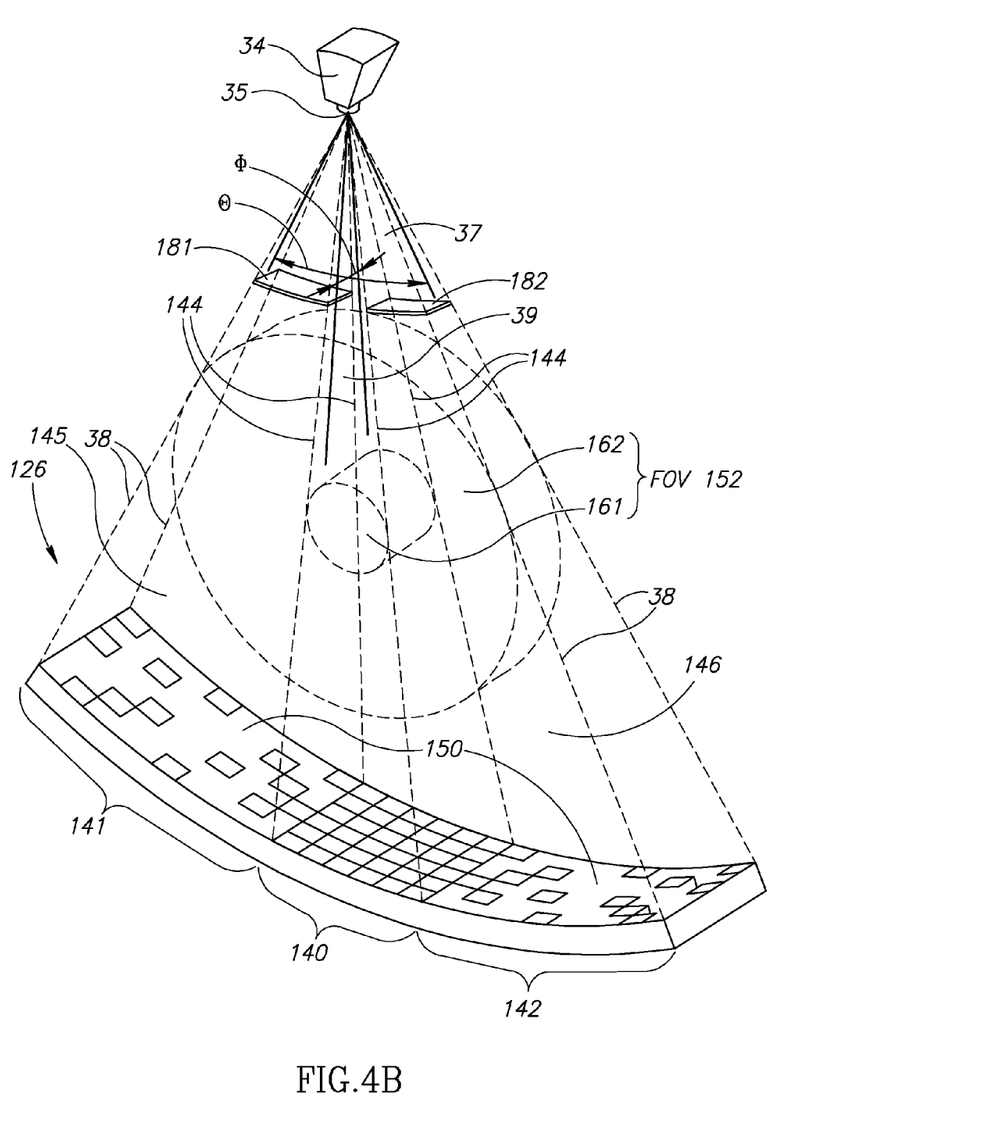

FIG. 4B schematically shows cone beam 38 shown in FIGS. 2A and 2B with detector array 126 being filtered by two optionally uniform thickness plate filters 181 and 182. Plate filters 161 and 162 filter side portions 145 and 146 of cone beam 38 respectively but, optionally do not filter central portion 144 of the beam. Optionally, plate filters attenuate side portions 141 and 146 by a factor greater than 10. Optionally, the plate filters are mounted in addition to butterfly filter. Optionally, the plate and butterfly filters attenuate the side portions by a factor greater than 50. Optionally, the plate and butterfly filters attenuate the side portions by a factor equal to about 100.

For CT scanners in accordance with an embodiment of the invention having a filtered beam, data acquired with filtered portions the beam is calibrated using methods known in the art to data acquired from unfiltered portions of the beam.

In the description and claims of the present application, each of the verbs, "comprise" "include" and "have", and conjugates thereof, are used to indicate that the object or objects of the verb are not necessarily a comprehensive listing of members, components, elements or parts of the subject or subjects of the verb.

The present invention has been described using detailed descriptions of embodiments thereof that are provided by way of example and are not intended to limit the scope of the invention. The described embodiments comprise different features, not all of which are required in all embodiments of the invention. Some embodiments of the invention utilize only some of the features or possible combinations of the features. Variations of the described embodiments and embodiments of the invention comprising different combinations of features noted in the described embodiments will occur to persons of the art. The scope of the invention is limited only by the following claims.

The invention claimed is:

1. A CT scanner comprising:
a rotor rotatable about an axis of rotation;
an X-ray source mounted to the rotor having a focal spot from which an X-ray beam emanates;
an X-ray detector array comprising a plurality of X-ray detectors for detecting X-rays in the X-ray beam that have been attenuated by an imaged body, wherein the detector array has at least one high resolution region in which the detector array has a high density and at least one low resolution region in which the detector array has a low density, and wherein the at least one low resolution area is displaced from the at least one high resolution area along a direction perpendicular to the axis of rotation; and
a processor adapted to reconstruct images for a portion of a body covered by the detector array high resolution region;
wherein said reconstruction includes processing of data for a portion of a body covered by the detector array low resolution region to estimate data that would be acquired for the body portion were the detector array low resolution region to have a resolution substantially equal to that of the detector array high resolution region.

2. The CT scanner in accordance with claim 1, wherein the reconstruction comprises back projection and wherein the processing of the data for the portion of the body covered by the detector array low resolution region includes completion of view data of the imaged body prior to the back projection.

3. The CT scanner in accordance with claim 1, wherein the high resolution region is flanked on both sides by low resolution regions.

4. The CT scanner in accordance with claim 3, wherein the detectors in the low resolution regions are arrayed in mirror image configurations.

5. The CT scanner in accordance with claim 1, wherein the detectors in the low resolution regions are arrayed so that areas of one of the low resolution regions that have detectors are homologous with areas of the other low resolution region that do not have detectors.

6. The CT scanner in accordance with claim 1, wherein size of the detectors is a function of distance from a sagittal plane that passes through the focal spot and axis of rotation and wherein detectors farther from the sagittal plane are larger than detectors closer to the plane.

7. The CT scanner in accordance with claim 1, wherein the high resolution region is flanked on one side by a single low resolution area.

8. The CT scanner in accordance with claim 1, wherein data acquired at a first view angle for a portion of a body covered by the detector array low resolution region at the first view angle and not covered by the detector array at the first view angle plus 180° is processed to estimate data for the portion of the body at the first view angle plus 180°.

9. The CT scanner in accordance with claim 1, wherein adjacent detectors in a low resolution region of the detector array are separated by insensitive regions having areas greater than or equal to about the size of the X-ray detectors.

10. The CT scanner in accordance with claim 1, wherein at least some of the detectors in the low resolution region are arrayed in incomplete rows and/or columns.

11. The CT scanner in accordance with claim 1, wherein adjacent detectors in a low resolution region of the detector array are separated by a distance greater than 0.3 mm.

12. The CT scanner in accordance with claim 1, wherein the CT scanner is a multislice scanner.

13. The CT scanner in accordance with claim 1, wherein the detectors in the high resolution and low resolution regions have substantially a same size.

14. The CT scanner in accordance with claim 1, wherein the detectors in the high resolution and low resolution regions have different sizes.

15. The CT scanner in accordance with claim 1, wherein the X-ray source and detector array define a field of view (FOV) for the scanner having a high resolution portion and a low resolution portion, wherein relatively high resolution attenuation data is acquired for a region of a patient imaged by the CT scanner that passes through the high resolution portion and relatively low resolution attenuation data is acquired for a region of the patient that passes through the low resolution portion of the FOV.

16. The CT scanner in accordance with claim 15, wherein the high resolution portion is defined by an area within a first circle having a first diameter and the low resolution portion is defined by an area between the first circle and a second circle having a second diameter that is concentric with the first circle.

17. The CT scanner in accordance with claim 16, wherein the first circle has a diameter less than or equal to 25 cm.

18. The CT scanner in accordance with claim 16, wherein the second circle has a diameter less than or equal to 50 cm.

19. The CT scanner in accordance with claim 1 and comprising X-ray radiation shielding that collimates X-rays from the X-ray source so that insensitive areas of the detector array are substantially not illuminated by X-rays.

20. A method for CT scanning, the method comprising:
providing an X-ray source mounted to a rotor having a focal spot from which an X-ray beam emanates, the rotor rotatable about an axis of rotation;
providing an X-ray detector array comprising a plurality of X-ray detectors for detecting X-rays in the X-ray beam that have been attenuated by an imaged body, wherein the detector array has at least one high resolution region in which the detector array has a high density and at least one low resolution region in which the detector array has a low density, wherein the at least one low resolution area is displaced from the at least one high resolution area along a direction perpendicular to the axis of rotation;
aligning a localized region of interest within a FOV of the at least one high resolution region of the detector array;
obtaining data from both the at least one low and the at least one high resolution region of the detector array; and
reconstructing images for the localized region of interest from data of both the at least one high and the at least one low resolution region of the detector array, wherein reconstructing images includes estimating data that would be acquired for the body region were the detector array at least one low resolution region to have a resolution substantially equal to that of the detector array in the at least one high resolution region.

21. The method in accordance with claim 20, wherein the high resolution region is flanked on both sides by a low resolution region.

22. The method in accordance with claim 20, wherein size of the detectors is a function of distance from a sagittal plane that passes through the focal spot and axis of rotation and wherein detectors farther from the sagittal plane are larger than detectors closer to the plane.

23. The CT scanner in accordance with claim 20, wherein the reconstruction comprises back projection and wherein the processing of the data for the portion of the body covered by the detector array low resolution region includes completion of view data of the imaged body prior to the back projection.

* * * * *